United States Patent [19]

Bauer

[11] Patent Number: 4,737,651
[45] Date of Patent: Apr. 12, 1988

[54] OPTICAL APPARATUS FOR THE MEASUREMENT OF COAT WEIGHT OF COATED PRODUCTS

[75] Inventor: George T. Bauer, Williamsville, N.Y.

[73] Assignee: Graphic Controls Corporation, Buffalo, N.Y.

[21] Appl. No.: 824,725

[22] Filed: Jan. 31, 1986

[51] Int. Cl.$^4$ ............................................. G01N 21/59
[52] U.S. Cl. ..................................... 250/571; 356/429; 356/433
[58] Field of Search ............... 250/571, 572, 559, 562, 250/563; 356/432, 433, 434, 429–431

[56] References Cited

U.S. PATENT DOCUMENTS

| | | | |
|---|---|---|---|
| 3,322,962 | 5/1967 | Muller | 250/571 |
| 3,632,226 | 1/1972 | Filby et al. | 250/559 |
| 3,827,808 | 8/1974 | Cho | 250/571 |

Primary Examiner—Edward P. Westin
Attorney, Agent, or Firm—Ratner & Prestia

[57] ABSTRACT

Optical apparatus which compares the transmittance of radiation through a coated product with the transmittance of radiation through only the base material of the coated product to measure the coating weight of the coating on the coated product. A dichroic filter or similar device is included to minimize or even eliminate radiation losses, due to reflections from the coated product, which affect the accuracy of the apparatus. The apparatus can be modified to measure selected characteristics of the base material instead of the coating.

12 Claims, 1 Drawing Sheet

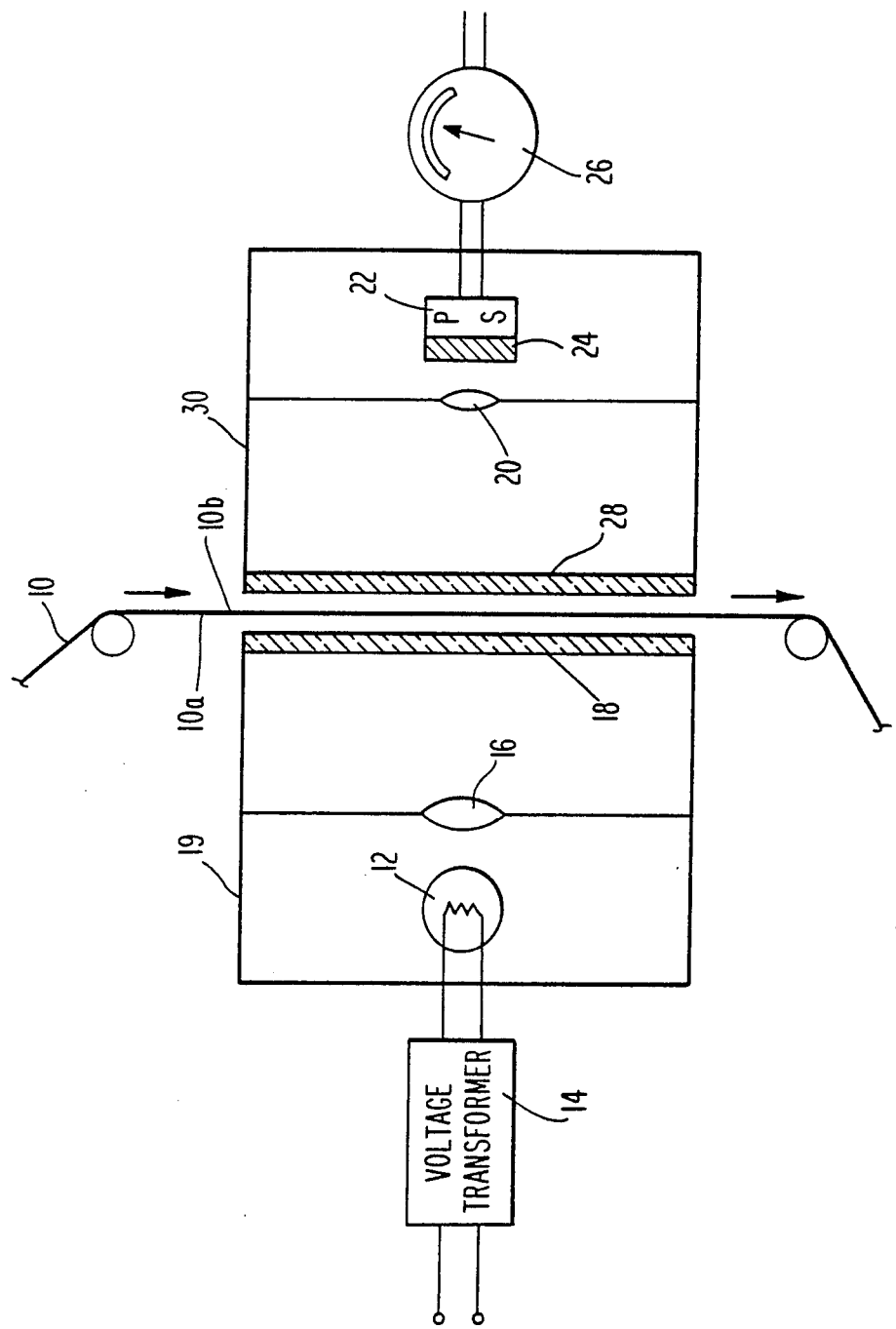

OPTICAL APPARATUS FOR THE MEASUREMENT OF COAT WEIGHT OF COATED PRODUCTS

TECHNICAL FIELD

The present invention relates, in general, to optical instrumentation and, in particular, to the analysis of coat weight of coated paper or other coated products by measuring the transmittance of light through the products being analyzed. Although the invention will be described in connection with the examination of a coating applied to a base paper, it will be apparent that the invention has other uses, such as analyzing the weight of base paper of a coated paper or coatings applied to other bases.

BACKGROUND ART

It is important, in the production of certain coated papers, that the coating be applied properly and to the correct degree. For example, if the coating on thermal paper used in copying machines is too thin, poor quality of the printed image results. Excessive thickness of the coating, while not necessarily producing an unfavorable effect on image quality, needlessly increases the cost of production.

Other aspects of coatings, besides thickness, also are of interest. Often, it is necessary for a coating to be applied uniformly. In certain applications, the positioning of coating segments is important.

In the production of coated paper products, the amount of coating material applied to the base paper is expressed as coating weight. Beta gauges are the most commonly used instruments for measuring the coating weight of a coated paper. Such instruments develop coating weight indications from the degree of absorption of beta rays by the coating.

Although in fairly widespread use, beta gauges suffer from certain shortcomings. Because beta rays are absorbed by water carried in the coated paper, the degree of absorption of beta rays is a function not only of the coat weight but of the water content as well. The water content of the coated paper should be measured separately and subtracted from the overall weight. Because the quantity indicated by beta gauges is directly proportional to the weight of the coating and of the base paper, the sensitivity and accuracy of beta gauges are limited when measuring thin coatings on relatively thick base papers.

DISCLOSURE OF THE INVENTION

Accordingly, it is an objective of the present invention to provide new and improved apparatus for analyzing the thickness or weight of coated products.

It is another objective of the present invention to provide apparatus for measuring the coating weight of coated paper and other coated products.

It is a further objective of the present invention to provide apparatus for analyzing selected characteristics of coated paper or other coated products which is relatively simple in construction, inexpensive to assemble, and easy to operate.

These and other objectives are achieved, in accordance with the present invention, by apparatus which includes lighting means for uniformly radiating a first surface of a coated product. The lighting means include a regulated light source and means for transmitting radiation from the light source to the first surface of the coated product and for reflecting back to this surface of the coated product radiation reflected by the coated product. The apparatus further includes measuring means for developing an indication of the transmittance of the coating on the coated product or the transmittance of the base material of the coated product, whichever is selected for analysis. The measuring means include imaging means for forming from the radiation passing through the coated product an image of a second surface of the coated product opposite from the first surface of the coated product. Also included in the measuring means are sensing means responsive to the image of the second surface of the coated product for developing a signal representative of the brightness of the image. The measuring means also include indicating means responsive to the signal developed by the sensing means and a reference signal representative of the brightness of radiation transmitted through only that component of the coated product not selected for analysis for developing an output indication representative of the transmittance of that component of the coated product selected for analysis. The apparatus further includes filter means disposed in the light path extending from the light source to the sensing means and having a transmittance characteristic which is low relative to the transmittance of that component of the coated product selected for analysis and high relative to the transmittance of the other component of the coated product for passing selected wavelengths of radiation corresponding to the transmittance characteristics of that component of the coated product selected for analysis.

BRIEF DESCRIPTION OF THE DRAWING

Referring to the drawing, the single figure is a schematic representation of a preferred embodiment of the present invention.

BEST MODE OF CARRYING OUT THE INVENTION

As shown in the drawing, apparatus for measuring the coating weight of a coated paper, constructed in accordance with the present invention, includes lighting means adapted to be positioned facing a first surface 10a of a coated paper 10 for uniformly radiating surface 10a. The lighting means include a regulated light source 12, such as a quartz-halogen lamp, which is powered through a constant voltage transformer 14 of conventional construction and operation.

The lighting means also include means for transmitting radiation from light source 12 to surface 10a of coated paper 10 and for reflecting back to surface 10a radiation reflected by coated paper 10. Such means may include a condenser lens 16 and a dichroic filter 18. Condenser lens 16, positioned between light source 12 and dichroic filter 18, functions in the usual way to gather as much of the radiation from light source 12 as possible and directs this radiation towards surface 10a of coated paper 10. Dichroic filter 18 forms a wall of a housing 19 containing light source 12 and condenser lens 16 and faces surface 10a of coated paper 10.

Dichroic filter 18, having a high transmittance and a high reflectance, passes radiation from light source 12 to surface 10a of coated paper 10 and reflects radiation reflected from the coated paper back to surface 10a of the coated paper. Because of the high reflectance of dichroic filter 18, radiation from light source 10 passing through the dichroic filter is forced through coated paper 10 and changes in the reflectance of coated paper 10, due to changes in the base paper or variations in the coating thickness, do not influence the operation of the apparatus.

The present invention also includes measuring means adapted to be positioned facing a second surface 10b of coated paper 10, opposite from surface 10a of the coated paper, for developing an indication of the transmittance of the coating on the coated paper. The measuring means include imaging means for forming from radiation passing through coated paper 10 an image of surface 10b of coated paper 10. The imaging means may include a lens 20 which produces a focussed image of surface 10b at the location of a photosensor 22, labelled in the drawing as PS, which, in response to the image, develops a signal representative of the brightness of the image.

Positioned between lens 20 and photosensor 22 is a filter 24. Filter 24 is interchangeable with other filters which have transmission peaks at various wavelengths, so that a variety of different coatings can be analyzed. A particular filter to be used has a transmittance characteristic which is high relative to the transmittance of the base paper of coated paper 10 and low relative to the transmittance of the coating on coated paper 10. This may be achieved most readily by selecting the peak transmission of the filter to fall within the 3700A–4500A range because within this range many types of optical whiteners used in various coatings have a generally high absorption. In order to provide fast changes of filters, they can be mounted on a turret.

Filter 24 serves to pass selected wavelengths of the image of surface 10b of the coated paper. In this way, variations in the characteristics of the base paper of the coated paper, which might otherwise affect the amount of radiation which passes through the coated paper, do not affect the brightness level of the selected wavelengths of the image which are passed by filter 24 to photosensor 22. In contrast, variations in the coating thickness or the uniformity of the coating on coated paper 10 show up as variations in the brightness of the selected wavelengths of the image passed by filter 24.

The signal developed by photosensor 22 is amplified electronically and then supplied to a suitable indicating device 26 which can be an analog or digital meter or a two-dimensional visual display. A second input to indicating device 26 is a reference signal which is representative of the brightness of radiation transmitted through only the base paper. Thus, indicating device 26 develops an output indication representative of the transmittance of radiation through the coated paper relative to the transmittance of radiation through only the base paper. The ratio of these two transmittances depends nearly linearly on the coating weight of the coated paper. A preferred way of developing the reference signal is to use a similar instrument, positioned before the coating station, so that the signal developed by the photosensor of this unit represents the transmittance of radiation through only the base paper. Before using the instrument for measuring weights of coatings, it is calibrated with a set of base papers coated with various thicknesses of the material to be measured.

Also included in the embodiment of the invention shown in the drawing is a clear glass plate 28. This glass plate, facing surface 10b of coated paper 10, forms a wall of a housing 30 which serves to protect lens 20, photosensor 22, and filter 24 from dust.

Instead of using a dichroic filter, an opal glass or a diffused glass can be used to transmit radiation from light source 12 and reflect back to surface 10a radiation reflected by coated paper 10. Also, the same effect can be achieved by painting white the wall of the housing within which the light source is contained, thereby providing an integrating cavity or by the combinations of the foregoing techniques.

It will be understood that a monochromator may be substituted for filter 24. Only that part of the image of surface 10b to whose wavelength the monochromator is set passes through the monochromator to photosensor 22.

Although filter 24 is shown positioned between lens 20 and photosensor 22 if the coating or the base paper is not luminescent, the filter may be positioned elsewhere in the light path extending from light source 12 to photosensor 22. For example, filter 24 can be located between condenser lens 16 and dichroic filter 18, in which case only the selected wavelengths passed by the filter are transmitted through coated paper 10. Also, filters can be placed in both positions, in which case the luminescence of the coating on the base paper does not influence the accuracy of the measurements.

For very thin coatings or in other extreme cases in which the transmittance of the coated paper is relatively high, trace amounts of absorbers, such as organic fluorescent material, can be added to the coating to enhance the effect and to improve the accuracy of the measurements. Another way of enhancing the effect is to measure the relative transmittance of multiple layers of the coated paper either by the use of mirrors which redirect the radiation to make multiple passes of radiation through the coated paper, or by routing the coated paper to make multiple passes through a single radiation path.

Finally, as already mentioned, the apparatus of the present invention can be used to measure the base paper weight rather than the coating weight. This can be accomplished by a different filter 24 which has a transmittance characteristic which is low relative to the transmittance of the base paper and high relative to the transmittance of the coating on the base paper. Furthermore, the apparatus of the present invention can be used to measure the coating weight of other coated products, so long as the base material is partially or fully transparent.

While in the foregoing there has been described a preferred embodiment of the invention, it should be understood to those skilled in the art that various modifications and changes can be made without departing from the true spirit and scope of the invention as recited in the claims.

What is claimed:
1. Apparatus for analyzing a coated product comprising:
   (a) lighting means for uniformly radiating a first surface of a coated product, said lighting means including:
      (1) a regulated light source, and
      (2) means for transmitting radiation from said light source to said first surface of said coated product and for reflecting back to said first surface radiation reflected by said coated product;
   (b) measuring means for developing an indication of the transmittance of the coating of said coated product or the transmittance of the base material of said coated product, whichever is selected for analysis, said measuring means including:
  (1) imaging means for forming from radiation passing through said coated product an image of a second surface of said coated product opposite from said first surface of said coated product,
  (2) sensing means responsive to said image of said second surface of said coated product for developing a signal representative of the brightness of said image, and
  (3) indicating means responsive to said sensing means signal and a reference signal representative of the brightness of radiation transmitted through only that component of said coated product not selected for analysis for developing an output indication representative of the transmittance of that component of said coated product selected for analysis; and
(c) means disposed in the light path extending from said light source to said sensing means and having a transmittance characteristic which is low relative to the transmittance of that component of said coated product selected for analysis and high relative to the transmittance of the other component of said coated product for filtering selected wavelengths of radiation.

2. Apparatus as defined by claim 1 wherein said transmittance characteristic of said filtering means is low relative to the transmittance of said coating of said coated product and high relative to the transmittance of said base material of said coated product.

3. Apparatus as defined by claim 2 wherein said lighting means are adapted to be positioned facing said first surface of said coated product and said measuring means are adapted to be positioned facing said second surface of said coated product.

4. Apparatus as defined by claim 3 wherein said transmitting and reflecting means include a condenser lens for gathering radiation from said light source.

5. Apparatus as defined by claim 4 wherein said filter means are positioned between said imaging means and said sensing means.

6. Apparatus as defined by claim 5 wherein said transmitting and reflecting means include a dichroic filter positioned on the opposite side of said condenser lens from said light source.

7. Apparatus as defined by claim 6 wherein said dichroic filter is a wall of a first housing containing said light source and condenser lens and faces said first surface of said coated product and said imaging means, sensing means and filtering means are contained in a second housing having a glass wall which faces said second surface of said coated product.

8. Apparatus for measuring the coating weight of a coated paper comprising:
  a regulated light source;
  means for transmitting radiation from said light source to a first surface of a coated paper to uniformly radiate said first surface and for reflecting back to said first surface radiation reflected by said coated paper;
  imaging means disposed on the opposite side of said coated paper from said light source for forming from radiation passing through said coated paper an image of a second surface of said coated paper opposite from said first surface of said coated paper;
  sensing means responsive to said image of said second surface of said coated paper for sensing the brightness of said image to develop a signal representative of the brightness of said image;
  filter means disposed in the light path extending from said light source to said sensing means for passing selected wavelengths of radiation from said light source, said filter means having a transmittance characteristic which is high relative to the transmittance of the base paper of said coated paper and low relative to the transmittance of the coating of said coated paper;
  and indicating means responsive to said sensing means signal and a reference signal representative of the brightness of radiation transmitted through only said base paper for developing an output indication representative of the transmittance of said coating.

9. Apparatus as defined by claim 8 wherein said filter means are positioned between said imaging means and said sensing means.

10. Apparatus as defined by claim 8 wherein said transmitting and reflecting means include a dichroic filter.

11. Apparatus as defined by claim 8 wherein said transmitting and reflecting means include a opal glass.

12. Apparatus as defined by claim 8 wherein said transmitting and reflecting means include a diffused glass.

* * * * *